(12) United States Patent
Stadler et al.

(10) Patent No.: US 9,731,138 B1
(45) Date of Patent: Aug. 15, 2017

(54) SYSTEM AND METHOD FOR CARDIAC PACING

(71) Applicant: Medtronic, Inc., Minneapolis, MN (US)

(72) Inventors: Robert W Stadler, Shoreview, MN (US); Zhongping Yang, Woodbury, MN (US); Sarah A Audet, Shoreview, MN (US); James K Carney, Roseville, MN (US); James D Reinke, Maple Grove, MN (US); Andrew J Ries, Lino Lakes, MN (US); John D Wahlstrand, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/141,430

(22) Filed: Apr. 28, 2016

Related U.S. Application Data

(60) Provisional application No. 62/296,398, filed on Feb. 17, 2016.

(51) Int. Cl.
*A61N 1/365* (2006.01)
*A61N 1/378* (2006.01)
*A61N 1/375* (2006.01)
*A61N 1/05* (2006.01)
*A61B 5/042* (2006.01)

(52) U.S. Cl.
CPC ........ *A61N 1/36585* (2013.01); *A61B 5/0422* (2013.01); *A61N 1/057* (2013.01); *A61N 1/36542* (2013.01); *A61N 1/3756* (2013.01); *A61N 1/3787* (2013.01)

(58) Field of Classification Search
CPC ...... A61N 1/362; A61N 1/3756; A61N 1/365; A61N 1/3787
See application file for complete search history.

(56) References Cited

U.S. PATENT DOCUMENTS

| 4,280,502 A | 7/1981 | Baker, Jr. et al. |
| 4,374,382 A | 2/1983 | Markowitz |
| 4,485,813 A | 12/1984 | Anderson et al. |
| 4,787,389 A | 11/1988 | Tarjan |

(Continued)

FOREIGN PATENT DOCUMENTS

| EP | 1541191 | 6/2005 |
| EP | 1961366 A1 | 8/2008 |

(Continued)

OTHER PUBLICATIONS

US 8,886,318, 11/2014, Jacobson et al. (withdrawn)

(Continued)

*Primary Examiner* — Michael Kahelin

(57) ABSTRACT

An implantable medical device system is configured to deliver cardiac pacing by receiving a cardiac electrical signal by sensing circuitry of a first device via a plurality of sensing electrodes, identifying by a control module of the first device a first cardiac event from the cardiac electrical signal, setting a first pacing interval in response to identifying the first cardiac event, controlling a power transmitter of the first device to transmit power upon expiration of the first pacing interval, receiving the transmitted power by a power receiver of a second device; and delivering at least a portion of the received power to a patient's heart via a first pacing electrode pair of the second device coupled to the power receiver.

40 Claims, 8 Drawing Sheets

(56) References Cited

U.S. PATENT DOCUMENTS

| | | |
|---|---|---|
| 4,830,006 A | 5/1989 | Haluska et al. |
| 4,865,037 A | 9/1989 | Chin et al. |
| 5,052,388 A | 10/1991 | Sivula et al. |
| 5,113,859 A | 5/1992 | Funke |
| 5,117,824 A | 6/1992 | Keimel et al. |
| 5,144,950 A | 9/1992 | Stoop et al. |
| 5,174,289 A | 12/1992 | Cohen |
| 5,193,539 A | 3/1993 | Schulman et al. |
| 5,243,976 A | 9/1993 | Ferek-Petric et al. |
| 5,255,692 A | 10/1993 | Neubauer et al. |
| 5,331,966 A | 7/1994 | Bennett et al. |
| 5,354,316 A | 10/1994 | Keimel |
| 5,402,070 A | 3/1995 | Shelton et al. |
| 5,411,535 A | 5/1995 | Fujii et al. |
| 5,545,185 A | 8/1996 | Denker |
| 5,620,474 A | 4/1997 | Koopman |
| 5,620,475 A | 4/1997 | Magnusson |
| 5,683,426 A | 11/1997 | Greenhut et al. |
| 5,749,909 A | 5/1998 | Schroeppel et al. |
| 5,814,089 A | 9/1998 | Stokes et al. |
| 5,817,130 A | 10/1998 | Cox et al. |
| 5,855,593 A | 1/1999 | Olson et al. |
| 5,861,018 A | 1/1999 | Feierbach |
| 5,893,882 A | 4/1999 | Peterson et al. |
| 5,897,583 A | 4/1999 | Meyer et al. |
| 5,928,271 A | 7/1999 | Hess et al. |
| 6,016,448 A | 1/2000 | Busacker et al. |
| 6,044,297 A | 3/2000 | Sheldon et al. |
| 6,108,579 A | 8/2000 | Snell et al. |
| 6,239,724 B1 | 5/2001 | Doron et al. |
| 6,256,534 B1 | 7/2001 | Dahl |
| 6,393,316 B1 | 5/2002 | Gillberg et al. |
| 6,411,842 B1 | 6/2002 | Cigaina et al. |
| 6,442,426 B1 | 8/2002 | Kroll |
| 6,477,420 B1 | 11/2002 | Struble et al. |
| 6,508,771 B1 | 1/2003 | Padmanabhan et al. |
| 6,522,915 B1 | 2/2003 | Ceballos et al. |
| 6,526,311 B2 | 2/2003 | Begemann |
| 6,592,518 B2 | 7/2003 | Denker et al. |
| 6,622,046 B2 | 9/2003 | Fraley et al. |
| 6,631,290 B1 | 10/2003 | Guck et al. |
| 6,738,668 B1 | 5/2004 | Mouchawar et al. |
| 6,754,528 B2 | 6/2004 | Bardy et al. |
| 6,788,971 B1 | 9/2004 | Sloman et al. |
| 6,904,315 B2 | 6/2005 | Panken et al. |
| 6,934,585 B1 | 8/2005 | Schloss et al. |
| 7,006,864 B2 | 2/2006 | Echt et al. |
| 7,031,772 B2 | 4/2006 | Condie et al. |
| 7,037,266 B2 | 5/2006 | Ferek-Petric et al. |
| 7,050,849 B2 | 5/2006 | Echt et al. |
| 7,181,284 B2 | 2/2007 | Burnes et al. |
| 7,184,830 B2 | 2/2007 | Echt et al. |
| 7,272,448 B1 | 9/2007 | Morgan et al. |
| 7,532,929 B2 | 5/2009 | Mussig et al. |
| 7,532,933 B2 | 5/2009 | Hastings et al. |
| 7,558,631 B2 | 7/2009 | Cowan et al. |
| 7,606,621 B2 | 10/2009 | Brisken et al. |
| 7,610,092 B2 | 10/2009 | Cowan et al. |
| 7,630,767 B1 | 12/2009 | Poore et al. |
| 7,634,313 B1 | 12/2009 | Kroll et al. |
| 7,680,538 B2 | 3/2010 | Durand et al. |
| 7,702,392 B2 | 4/2010 | Echt et al. |
| 7,702,395 B2 | 4/2010 | Towe et al. |
| 7,706,879 B2 | 4/2010 | Burnes et al. |
| 7,742,812 B2 | 6/2010 | Ghanem et al. |
| 7,742,816 B2 | 6/2010 | Masoud et al. |
| 7,751,881 B2 | 7/2010 | Cowan et al. |
| 7,765,001 B2 | 7/2010 | Echt et al. |
| 7,809,438 B2 | 10/2010 | Echt et al. |
| 7,848,815 B2 | 12/2010 | Brisken et al. |
| 7,881,791 B2 | 2/2011 | Sambelashvili et al. |
| 7,890,173 B2 | 2/2011 | Brisken et al. |
| 7,894,904 B2 | 2/2011 | Cowan et al. |
| 7,894,907 B2 | 2/2011 | Cowan et al. |
| 7,894,910 B2 | 2/2011 | Cowan et al. |
| 7,899,541 B2 | 3/2011 | Cowan et al. |
| 7,899,542 B2 | 3/2011 | Cowan et al. |
| 7,904,153 B2 | 3/2011 | Greenhut et al. |
| 7,930,027 B2 | 4/2011 | Prakash et al. |
| 7,937,148 B2 | 5/2011 | Jacobson |
| 7,937,159 B2 | 5/2011 | Lima et al. |
| 7,941,218 B2 | 5/2011 | Sambelashvili et al. |
| 7,949,404 B2 | 5/2011 | Hill |
| 7,953,493 B2 | 5/2011 | Fowler et al. |
| 7,991,467 B2 | 8/2011 | Markowitz et al. |
| 7,996,087 B2 | 8/2011 | Cowan et al. |
| 8,002,718 B2 | 8/2011 | Buchholtz et al. |
| 8,032,219 B2 | 10/2011 | Neumann et al. |
| 8,078,283 B2 | 12/2011 | Cowan et al. |
| 8,145,308 B2 | 3/2012 | Sambelashvili et al. |
| 8,160,684 B2 | 4/2012 | Ghanem et al. |
| 8,204,590 B2 | 6/2012 | Sambelashvili et al. |
| 8,214,041 B2 | 7/2012 | Van Gelder et al. |
| 8,249,717 B2 | 8/2012 | Brockway et al. |
| 8,265,770 B2 | 9/2012 | Toy et al. |
| 8,315,701 B2 | 11/2012 | Cowan et al. |
| 8,332,036 B2 | 12/2012 | Hastings et al. |
| 8,340,773 B2 | 12/2012 | Towe et al. |
| 8,364,276 B2 | 1/2013 | Willis |
| 8,369,956 B2 | 2/2013 | Towe et al. |
| 8,386,048 B2 | 2/2013 | McClure et al. |
| 8,391,964 B2 | 3/2013 | Musley et al. |
| 8,428,716 B2 | 4/2013 | Mullen et al. |
| 8,433,409 B2 | 4/2013 | Johnson et al. |
| 8,457,742 B2 | 6/2013 | Jacobson |
| 8,478,408 B2 | 7/2013 | Hastings et al. |
| 8,494,637 B2 | 7/2013 | Cowan et al. |
| 8,494,639 B2 | 7/2013 | Cowan et al. |
| 8,494,642 B2 | 7/2013 | Cowan et al. |
| 8,494,643 B2 | 7/2013 | Cowan et al. |
| 8,494,644 B2 | 7/2013 | Cowan et al. |
| 8,498,715 B2 | 7/2013 | Cowan et al. |
| 8,521,268 B2 | 8/2013 | Zhang et al. |
| 8,532,785 B1 | 9/2013 | Crutchfield et al. |
| 8,541,131 B2 | 9/2013 | Lund et al. |
| 8,588,909 B1 | 11/2013 | Levine |
| 8,588,926 B2 | 11/2013 | Moore et al. |
| 8,617,082 B2 | 12/2013 | Zhang et al. |
| 8,626,303 B2 | 1/2014 | Towe et al. |
| 8,630,716 B2 | 1/2014 | Brockway et al. |
| 8,630,717 B2 | 1/2014 | Olson et al. |
| 8,634,908 B2 | 1/2014 | Cowan |
| 8,639,333 B2 | 1/2014 | Stadler et al. |
| 8,718,773 B2 | 5/2014 | Willis et al. |
| 8,744,572 B1 | 6/2014 | Greenhut et al. |
| 8,768,459 B2 | 7/2014 | Ghosh |
| 8,774,928 B2 | 7/2014 | Towe et al. |
| 8,886,307 B2 | 11/2014 | Sambelashvili et al. |
| 8,886,311 B2 | 11/2014 | Anderson et al. |
| 8,909,351 B2 | 12/2014 | Dinsmoor et al. |
| 8,923,963 B2 | 12/2014 | Bonner et al. |
| 8,996,109 B2 | 3/2015 | Karst et al. |
| 9,008,776 B2 | 4/2015 | Cowan et al. |
| 9,014,803 B2 | 4/2015 | Cowan |
| 9,072,911 B2 | 7/2015 | Hastings et al. |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,278,218 B2 | 3/2016 | Karst et al. |
| 2002/0091421 A1 | 7/2002 | Greenberg et al. |
| 2004/0204744 A1 | 10/2004 | Penner et al. |
| 2004/0215308 A1 | 10/2004 | Bardy et al. |
| 2005/0197680 A1 | 9/2005 | DelMain et al. |
| 2005/0277990 A1 | 12/2005 | Ostroff et al. |
| 2006/0009818 A1 | 1/2006 | Von Arx et al. |
| 2006/0031378 A1 | 2/2006 | Vallapureddy et al. |
| 2006/0085041 A1 | 4/2006 | Hastings et al. |
| 2006/0149329 A1 | 7/2006 | Penner |
| 2006/0161061 A1 | 7/2006 | Echt et al. |
| 2006/0161205 A1 | 7/2006 | Mitrani et al. |
| 2006/0206165 A1 | 9/2006 | Jaax et al. |
| 2006/0235478 A1 | 10/2006 | Van Gelder et al. |
| 2006/0241705 A1 | 10/2006 | Neumann et al. |
| 2007/0049975 A1 | 3/2007 | Cates et al. |

(56) References Cited

U.S. PATENT DOCUMENTS

| | | |
|---|---|---|
| 2007/0088394 A1 | 4/2007 | Jacobson |
| 2007/0088398 A1 | 4/2007 | Jacobson |
| 2007/0106143 A1 | 5/2007 | Flaherty |
| 2007/0293900 A1 | 12/2007 | Sheldon et al. |
| 2008/0046038 A1 | 2/2008 | Hill et al. |
| 2008/0154322 A1 | 6/2008 | Jackson et al. |
| 2008/0269816 A1 | 10/2008 | Prakash et al. |
| 2008/0269823 A1 | 10/2008 | Burnes et al. |
| 2009/0036940 A1 | 2/2009 | Wei et al. |
| 2009/0036941 A1 | 2/2009 | Corbucci |
| 2009/0105782 A1 | 4/2009 | Mickle et al. |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2010/0016911 A1 | 1/2010 | Willis et al. |
| 2010/0016914 A1 | 1/2010 | Mullen et al. |
| 2010/0023078 A1 | 1/2010 | Dong et al. |
| 2010/0042108 A1 | 2/2010 | Hibino |
| 2010/0152798 A1 | 6/2010 | Sanghera et al. |
| 2010/0198291 A1 | 8/2010 | Sambelashvili et al. |
| 2010/0228308 A1 | 9/2010 | Cowan et al. |
| 2010/0286541 A1 | 11/2010 | Musley et al. |
| 2010/0286744 A1 | 11/2010 | Echt et al. |
| 2011/0071586 A1 | 3/2011 | Jacobson |
| 2011/0184492 A1 | 7/2011 | Martens et al. |
| 2011/0190841 A1 | 8/2011 | Sambelashvili et al. |
| 2011/0196444 A1 | 8/2011 | Prakash et al. |
| 2011/0224744 A1 | 9/2011 | Moffitt et al. |
| 2011/0237967 A1 | 9/2011 | Moore et al. |
| 2012/0008714 A1 | 1/2012 | Rizwan |
| 2012/0035685 A1 | 2/2012 | Saha et al. |
| 2012/0109235 A1 | 5/2012 | Sheldon et al. |
| 2012/0109236 A1 | 5/2012 | Jacobson et al. |
| 2012/0172892 A1 | 7/2012 | Grubac et al. |
| 2012/0263218 A1 | 10/2012 | Dal Molin et al. |
| 2012/0296228 A1 | 11/2012 | Zhang et al. |
| 2012/0316613 A1 | 12/2012 | Keefe et al. |
| 2013/0013017 A1 | 1/2013 | Mullen et al. |
| 2013/0066169 A1 | 3/2013 | Rys et al. |
| 2013/0116738 A1 | 5/2013 | Samade et al. |
| 2013/0131750 A1 | 5/2013 | Stadler et al. |
| 2013/0131751 A1 | 5/2013 | Stadler et al. |
| 2013/0197599 A1 | 8/2013 | Sambelashvili et al. |
| 2013/0231710 A1 | 9/2013 | Jacobson |
| 2013/0268017 A1 | 10/2013 | Zhang et al. |
| 2013/0274828 A1 | 10/2013 | Willis |
| 2013/0282027 A1 | 10/2013 | Woodard, Jr. et al. |
| 2013/0282073 A1 | 10/2013 | Cowan et al. |
| 2014/0046420 A1 | 2/2014 | Moore et al. |
| 2014/0114372 A1 | 4/2014 | Ghosh et al. |
| 2014/0121720 A1 | 5/2014 | Bonner et al. |
| 2014/0207210 A1 | 7/2014 | Willis et al. |
| 2014/0330208 A1 | 11/2014 | Christie et al. |
| 2014/0330287 A1 | 11/2014 | Thompson-Nauman et al. |
| 2014/0330326 A1 | 11/2014 | Thompson-Nauman et al. |
| 2014/0358135 A1 | 12/2014 | Sambelashvili et al. |
| 2015/0100110 A1 | 4/2015 | Towe et al. |
| 2015/0112233 A1 | 4/2015 | Towe et al. |
| 2015/0142070 A1 | 5/2015 | Sambelashvili |
| 2015/0196755 A1 | 7/2015 | Cowan |
| 2015/0265841 A1 | 9/2015 | Min et al. |
| 2015/0321011 A1 | 11/2015 | Carney et al. |
| 2015/0321012 A1 | 11/2015 | Cinbis et al. |
| 2015/0321016 A1 | 11/2015 | O'Brien et al. |
| 2016/0001086 A1 | 1/2016 | Towe et al. |
| 2016/0035967 A1 | 2/2016 | Moore et al. |

FOREIGN PATENT DOCUMENTS

| | | |
|---|---|---|
| EP | 2471452A1 A1 | 7/2012 |
| WO | 95/02995 | 2/1995 |
| WO | 2004002572 A1 | 1/2004 |
| WO | 2004/078252 A2 | 9/2004 |
| WO | 2006069215 A2 | 6/2006 |
| WO | 2006/133554 A1 | 12/2006 |
| WO | 2009006531 A1 | 1/2009 |

OTHER PUBLICATIONS

Greenhut, et al., Method and Apparatus for Selection and Use of Virtual Sensing Vectors, U.S. Appl. No. 14/524,090, filed Oct. 27, 2014, 57pp.

(PCT/US2015/029458) PCT Notification of Transmittal of the International Search Report and the Written Opinion of the International Searching Authority, mailed Aug. 25, 2015, 8 pages.

(PCT/US2015/029464) PCT Notification of Transmittal of the International Search Report and the Written Opinion of the International Searching Authority, Mailed Jul. 13, 2015, 9 pages.

(PCT/US2014/066792) PCT Notification of Transmittal of the International Search Report and the Written Opinion of the International Searching Authority.

(PCT/US2013/013601) PCT Notification of Transmittal of the International Search Report and the Written Opinion of the International Searching Authority.

Rodney Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.

U.S. Appl. No. 14/801,049, filed Jul. 16, 2015.

(PCT/US2014/036782) PCT Notification of Transmittal of the International Search Report and the Written Opinion of the International Searching Authority, Mailed Aug. 22, 2014, 12 pages.

Ganapathy et al., "Implantable Device to Monitor Cardiac Activity with Sternal Wires," Pace, vol. 37, Dec. 2014, 11 pages.

Guenther et al., "Substernal Lead Implantation: A Novel Option to Manage DFT Failure in S-ICD patients," Clinical Research Cardiology, Published On-line Oct. 2, 2014, 3 pages.

Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.

(PCT/U52017/016245) PCT Notification of Transmittal of the International Search Report and the Written Opinion of the International Searching Authority, dated May 9, 2017, 11 pages.

SYSTEM AND METHOD FOR CARDIAC PACING

CROSS-REFERENCE TO RELATED APPLICATIONS

This application claims the benefit of U.S. Provisional Application No. 62/296,398, filed on Feb. 17, 2016. The disclosure of the above application is incorporated herein by reference in its entirety.

TECHNICAL FIELD

The disclosure relates generally to implantable medical devices and, in particular, to a system and method for delivering cardiac pacing without transvenous leads.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Conduction defects may occur along the intrinsic conduction pathways of the heart leading to irregularities in heart rate and asynchrony between heart chambers. Cardiac pacemakers are available to deliver electrical pacing pulses to one or more heart chambers to restore a more normal heart rhythm. Cardiac pacemakers may be coupled to one or more medical electrical leads to position electrodes at desired pacing sites, e.g., at endocardial pacing sites or within a cardiac vein. Single chamber leadless pacemakers have been proposed that carry electrodes on the housing of the pacemaker and may be implanted in a heart chamber without requiring a transvenous lead. The single chamber leadless pacemaker may sense cardiac electrical signals that indicate depolarization of the heart chamber in which the pacemaker is implanted and deliver pacing pulses in the same cardiac chamber.

DETAILED DESCRIPTION

In the following description, references are made to illustrative embodiments for carrying out the methods described herein. It is understood that other embodiments may be utilized without departing from the scope of the disclosure.

Figure 1:
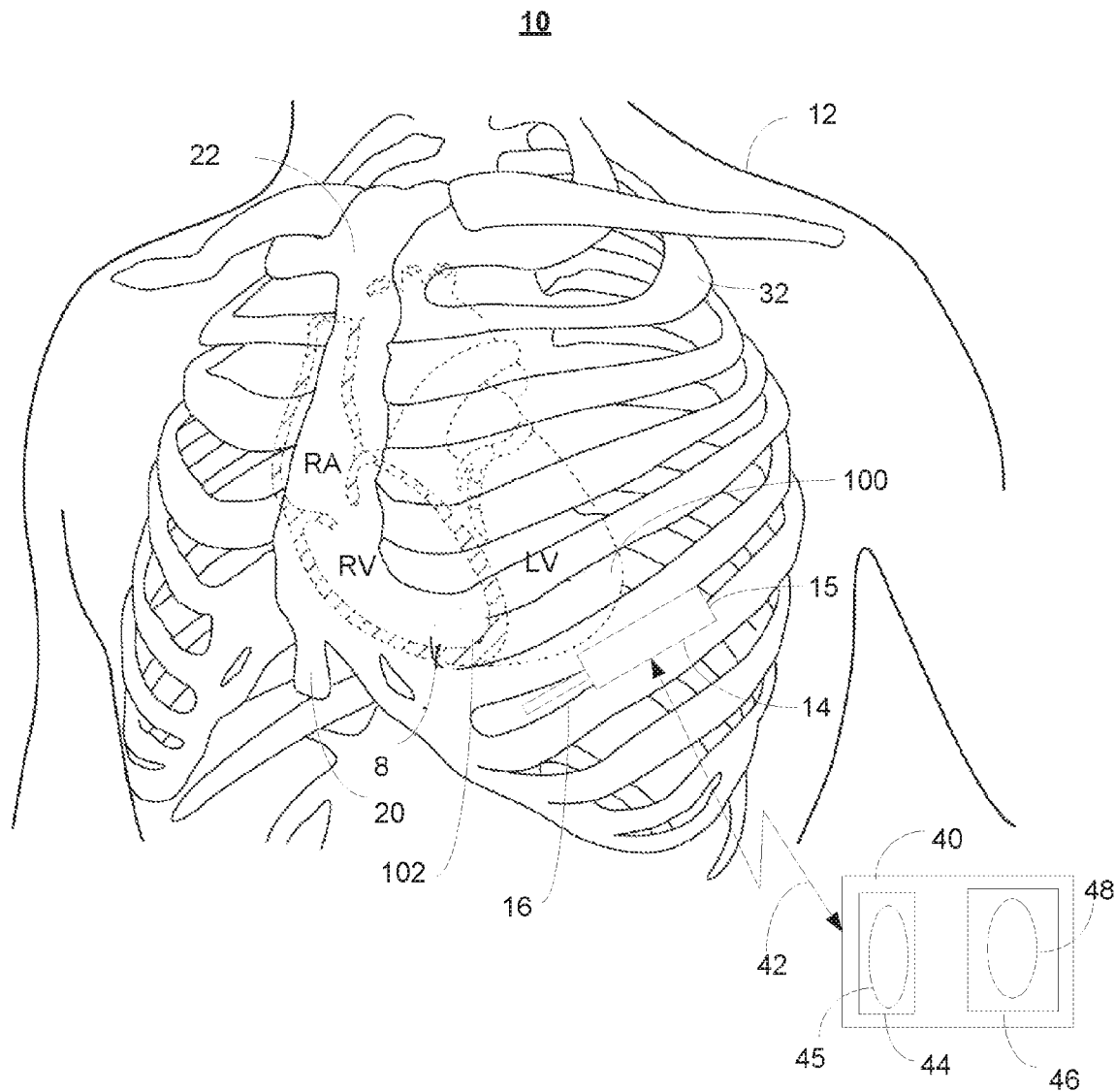
FIG. 1 is a conceptual diagram of an implantable medical device (IMD) system for delivering cardiac pacing according to one example.

FIG. 1 is a conceptual diagram of an implantable medical device (IMD) system 10 for delivering cardiac pacing according to one example. IMD system 10 includes a sensing device 14 and a pulse delivery device 100. Sensing device 14 is implanted outside the cardiovascular system, e.g., subcutaneously, submuscularly, or substernally, and includes a housing 15 that encloses internal circuitry of sensing device 14, e.g., cardiac electrical sensing circuitry, a primary and/or rechargeable battery, electromechanical and/or thermal sensors to generate a signal correlated to patient activity, posture, temperature or other parameters used for controlling the timing and rate of pacing pulses, and power-transmitting circuitry as described below in conjunction with FIG. 3. Sensing device 14 may include one or more housing-based electrodes and/or an electrode extension 16 extending from housing 15 for carrying one or more electrodes for sensing cardiac electrical signals produced by the patient's heart 8, e.g., P-waves attendant to the depolarization of the atria of heart 8 and/or R-waves attendant to the depolarization of the ventricles of heart 8.

Pulse delivery device 100 is a miniaturized device configured to harvest power transmitted by sensing device 15 and deliver at least a portion of the transmitted power as a pacing pulse to heart 8 to cause an evoked depolarization of the myocardium. As described in conjunction with FIG. 5, pulse delivery device 100 includes a housing, a housing-based pacing electrode pair, a power receiver coupled to the housing based electrodes, and a power harvesting circuit for coupling at least a portion of received power to a cathode electrode of the pacing electrode pair to deliver the received power in the form of a pacing pulse to capture the patient's heart 8.

Sensing device 14 is configured to sense a cardiac electrical signal, identify cardiac events from the cardiac electrical signal and control a power transmitter to transmit a power signal to pulse delivery device 100. Sensing device 14 transmits the power signal to pulse delivery device 100 at an appropriate pacing interval following a cardiac event, e.g., following a P-wave or an R-wave, or following a preceding pacing pulse, to restore a more normal heart rhythm and/or cardiac chamber synchrony, e.g., when a conduction defect, atrial arrhythmia or other heart rhythm abnormality is present. Sensors incorporated in sensing device 14 may be used in determining the timing of the power transmission, monitor sensing device temperature, and/or monitor the patient's physiologic status.

In some examples, system 10 may include multiple pulse delivery devices, e.g., pulse delivery device 100 and pulse delivery device 102. In the example shown, pulse delivery device 100 is deployed along the left ventricle 9 of heart 8 for pacing the left ventricle. Pulse delivery device 100 may be deployed within a cardiac vein using a transvenous approach via the right atrium and coronary sinus. In other examples, pulse delivery device 100 may be implanted within the left ventricle (LV) along the endocardium or implanted epicardially, e.g., along the anterior, posterior, or lateral free wall or apex of the left ventricle. Pulse delivery device 102 is shown deployed along the right ventricle (RV) of the patient's heart 8 in the example of FIG. 1. Pulse delivery device 102 may be implanted endocardially using a transvenous approach via the right atrium (RA) at or near the right ventricular apex.

Pulse delivery devices 100 and 102 may include an active or passive fixation member, such as a single- or multi-tined fixation member, a hook, a helical screw, or other member that passively or actively engages with tissue at a target implant site, e.g., with the ventricular trabeculae, endocardium, epicardium, or cardiac vein inner walls. Pulse delivery device 100 is deployed and anchored at a first pacing site, e.g., along the left ventricle, and pulse delivery device 102 is deployed and anchored at a second pacing site spaced apart from the first pacing site, which may be in the same cardiac chamber such as the left ventricle, or a different cardiac chamber such as the right ventricle. The locations of pulse delivery devices 100 and 102 in FIG. 1 are illustrative in nature and not intended to be limiting.

In the illustrative examples presented herein, pulse delivery device 100 is described as being deployed for delivering LV pacing pulses. However, pulse delivery devices 100 and 102 are not limited to ventricular pacing applications. In other examples, a pulse delivery device 100 may be deployed in, along our outside an atrial chamber or a ventricular chamber for delivering cardiac pacing pulses. In still other examples, pulse delivery device 100 is not limited to delivering cardiac pacing pulses and may be positioned along a nerve or other excitable tissue for delivering a neurostimulation therapy, such as along the spinal cord, vagal nerve, phrenic nerve, a skeletal muscle nerve, sensory nerve, brain, etc.

Sensing device 14 is deployed to an extra-cardiovascular location selected to enable acquisition of a cardiac electrical signal with acceptable signal-to-noise ratio for processing and analysis that allows reliable sensing and identification of cardiac events, e.g., at least R-waves, at least P-waves and R-waves, or at least P-waves, R-waves and T-waves. The implant location of sensing device 14 is also selected to enable acceptable power transmission efficiency to at least pulse delivery device 100 and pulse delivery device 102 if present. In other examples, multiple sensing devices may be implanted at extra-cardiovascular locations, each paired with a designated pulse delivery device 100 or 102. The separate implantation sites of each of the multiple sensing devices may be selected to provide optimal sensing of cardiac events used to set pacing timing intervals for controlling power transmission time to the respective pulse delivery device and to provide acceptable power transmission efficiency to the respective pulse delivery device.

For example, if sensing device 14 is implanted subcutaneously along a left intercostal space of ribcage 32 for transmitting power to pulse delivery device 100 positioned along the LV, a second sensing device may be implanted for transmitting power to pulse delivery device 102 implanted along the RV. The second sensing device may be implanted substernally, subcutaneously along a right intercostal space, or subcutaneously along a left intercostal space but medially, superiorly or inferiorly to sensing device 14. When more than one sensing device is included in system 10, the multiple sensing devices may be positioned along a common intercostal space but at different medial or lateral locations or along different intercostal spaces at the same or different medial or lateral locations.

Sensing extension 16 is provided to extend at least one electrode away from housing 15 to provide a sensing vector having greater inter-electrode spacing and having an angle relative to the heart axis that maximizes the signal strength of desired cardiac events, e.g., P-waves. Sensing extension 16 may be provided as a removable or non-removable member of sensing device 14 but may be coupled to sensing device 14 prior to implantation to provide one-step placement of sensing device 14 with sensing extension 16 already fixedly attached to housing 15, e.g., via a coupling member.

Figure 3:
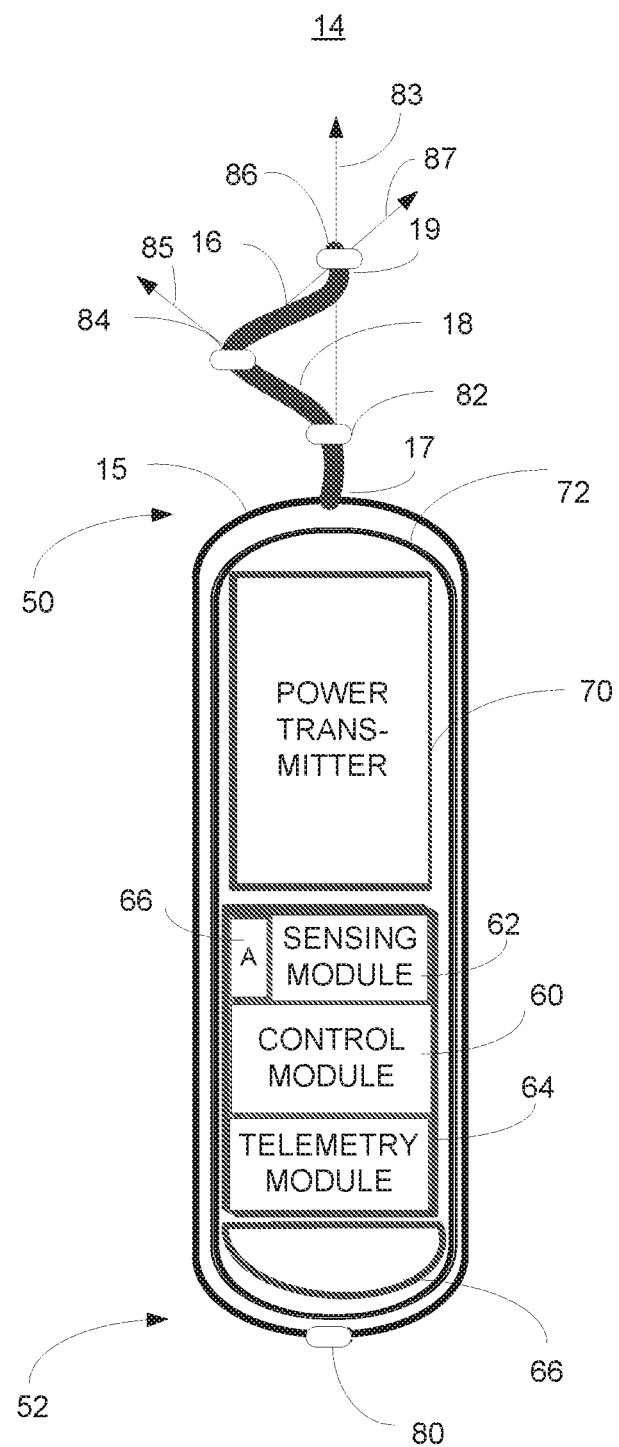
FIG. 3 is a schematic diagram of the sensing device of FIG. 1 according to one example.
Figure 4:
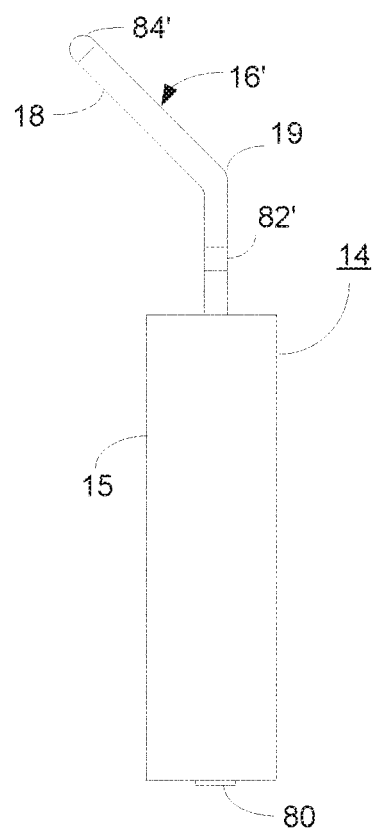
FIG. 4 is a schematic diagram of the sensing device of FIG. 1 having an alternative sensing extension.

For example, sensing device 14 and extension 16 may be implanted as a singular unit via an open incision at the desired implant site or advanced to and released at the implant site using a delivery tool such as a catheter or guide wire to enable a small incision and minimal invasiveness of the implant procedure. While sensing extension 16 is shown as a linear extension in the example of FIG. 1, other examples of non-linear sensing extensions including one or more bends or curves are shown in FIGS. 3 and 4.

System 10 may further include an external device 40 configured to transmit programming commands to sensing device 14 via wireless telemetry and receive data from sensing device 14. In some examples, sensing device 14 is a rechargeable device including one or more rechargeable batteries that are charged by external device 40. In such examples, external device 40 includes a power transmitter 46 including a regulated power source and a coil 48 for inductive power transfer via radio frequency (RF) coupling between primary coil 48 and a secondary coil included in sensing device 14. A power receiver in sensing device 14 receives the transmitted power and harvests at least a portion of the power for recharging the battery(ies). In some examples, a coil or transducer used for transmitting power from sensing device 14 to pulse delivery device 100 is also configured to receive power from external device 40.

Sensing device 14 is a programmable device including a telemetry circuit for sending and receiving data to external device 40. External device 40 is shown in telemetric communication with sensing device 14 by a communication link 42. External device 40 may include a processor; computer-readable storage media such as RAM, ROM, flash storage or other storage media; a display; a user interface; a telemetry unit 44 including a communication antenna or coil 45 for telemetric communication with sensing device 14 via communication link 42, and a power transmitter 46 including a primary coil 48 for transmitting RF energy to sensing device 14 at a selected resonant frequency separated from the communication frequency used by the telemetry unit antenna 45.

External device 40 communicates with sensing device 14 for transmitting and receiving data via communication link 42. Communication link 42 may be established between sensing device 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from sensing device 14 and to program operating parameters and algorithms in sensing device 14 for controlling sensing and power transmission functions. External device 40 may be used to program cardiac event sensing parameters and power signal transmission control parameters used by sensing device 14 to control the timing and strength of power transmission to pulse delivery device 100, thereby controlling the timing and available energy for delivering pacing pulses by pulse delivery device 100.

Data stored or acquired by sensing device 14, including cardiac electrical signals, power transmission history, detected pacing pulses delivered by pulse delivery device 100, activity, posture, temperature, physiologic status, etc. or associated data derived therefrom, may be retrieved from sensing device 14 by external device 40 using an interrogation command. External device 40 may alternatively be embodied as a home monitor, bedside or hand-held device and used for recharging one or more batteries of sensing device 14, programming sensing device 14, and retrieving data from sensing device 14. Pulse delivery devices 100 and 102 may have no or limited communication capabilities. In other examples, pulse delivery devices 100 and 102 may be configured for bi-directional communication with external device 40 and/or sensing device 14.

Figure 2A:
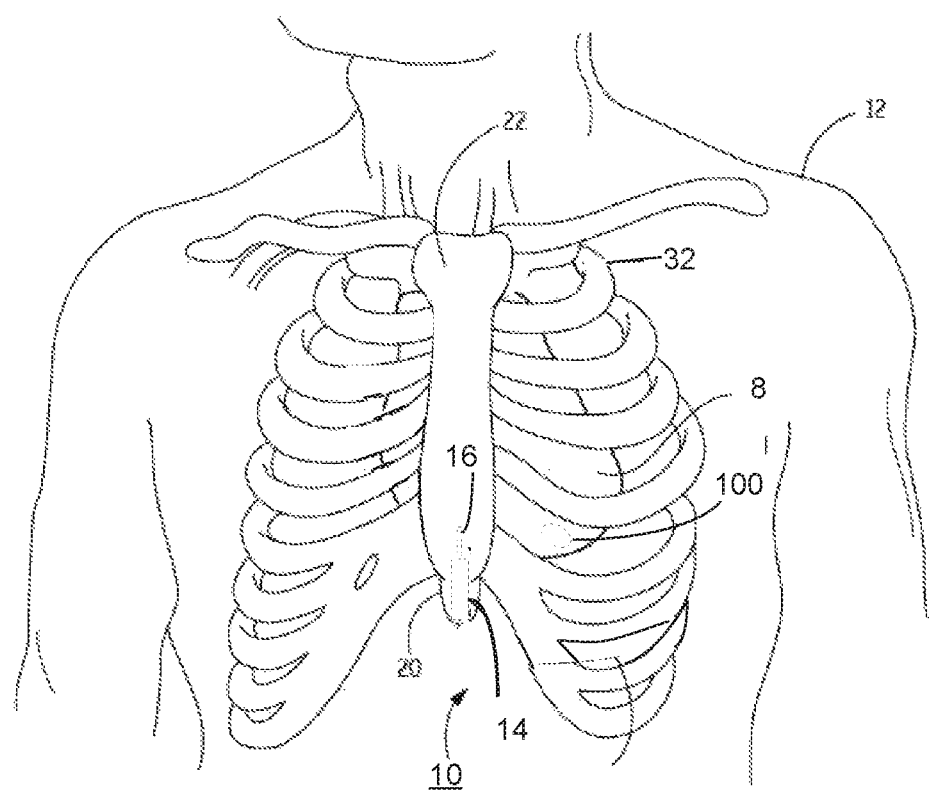
FIG. 2A is a front view and FIG. 2B is a side view of an implantable cardiac pacing system having a sensing device deployed at least partially substernally within a patient.
Figure 2B:
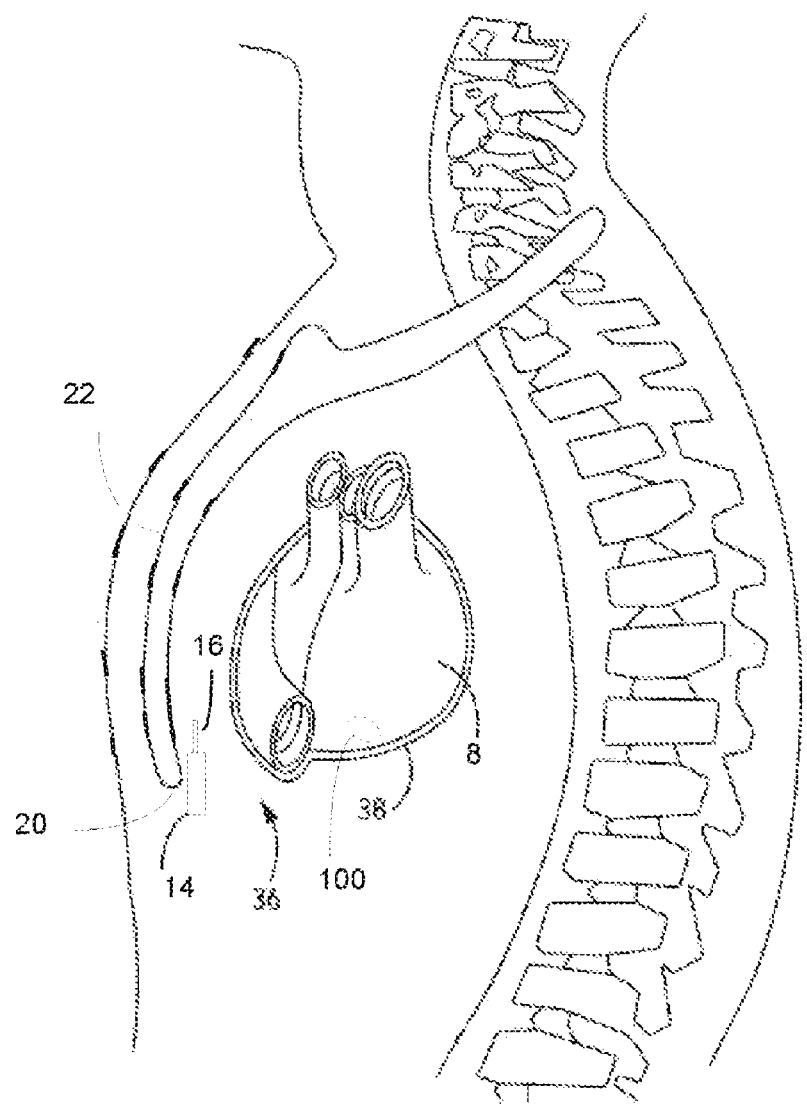

FIG. 2A is a front view of an implantable cardiac pacing system 10 in which sensing device 14 is shown implanted at least partially substernally within patient 12. FIG. 2B is a side view of sensing device 14 implanted substernally within patient 12. Pulse delivery device 100 is shown positioned along the left ventricle of heart 8, e.g., along a cardiac vein, epicardially, within or along the pericardium 38, or endocardially. Sensing device 14 may be implanted so that all or a portion of sensing extension 16 extends beneath sternum 22. Housing 15 of sensing device 14 may be positioned entirely beneath sternum 22, e.g., along the anterior mediastinum 36. In other examples, sensing device 14 may be implanted such that housing 15 is adjacent to or inferior to xiphoid process 20 with sensing extension extending superiorly beneath sternum 22.

Sensing device 14 is shown extending approximately parallel with sternum 22 but may extend in an at least a partially substernal position at an angle relative to sternum 22, e.g., with sensing extension 16 directed at an angle laterally to the left or the right of sternum 22. In other examples, sensing device 14 or at least a portion of sensing extension 16 may be implanted partially beneath ribcage 32.

FIG. 3 is a schematic diagram of sensing device 14 according to one example. Sensing device housing 15 encloses circuitry including a sensing module 62, a control module 60, and a telemetry module 64, all of which may be in the form of an integrated circuit coupled to a battery 66 for providing power to the components of the integrated circuit as needed. Battery 66 may include one or more rechargeable and/or non-rechargeable battery cells. In one example, battery 66 or another charge storage device is recharged via current induced on coil 72 via power transmitted by external device 40 (FIG. 1).

As described above, power may be transmitted to recharge battery 66 by RF coupling between a primary coil 48 included in external device 40 and secondary, induction coil 72 included in sensing device 14 for receiving power transmitted from external device 40. Secondary coil 72 may be additionally be coupled to telemetry module 64 to function as an antenna for communication telemetry with external device 40 depending on the communication telemetry frequency being used. Sensing device 14 may include a single coil 72 and decode circuitry to separate RF telemetry communication signals received from external device 40 from RF coupled power transmission from external device 40 for recharging battery 66.

Control module 60 may be configured to monitor the charge of battery 66 and transmit a signal via telemetry module 64 to external device 40 to signal when a recharge of battery 66 is required. During recharging, control module 60 may monitor the battery charge and control telemetry module 64 to transmit a signal when battery 66 is fully charged, and recharging is complete. Examples of an implantable medical device with a rechargeable battery and associated recharging methods are generally disclosed in U.S. Pat. No. 8,909,351 (Dinsmoore, et al.) and U.S. Pat. No. 8,630,717 (Olson, et al.), both of which are incorporated herein by reference in their entirety.

Housing 16 also encloses a power transmitter circuit 70 for transmitting power to pulse delivery device 100. In some examples, a second coil may be provided for RF power transmission from sensing device 14 to pulse delivery device 100 when power transmitter circuit 70 is configured to generate and control RF power transmission signals. In other examples, sensing device includes a single coil 72 for receiving power transmission from external device 40 for recharging battery 66, and power transmitter circuit 70 is configured as an acoustic power transmitter including ultrasonic transducers, such as piezoelectric transducers, for transmitting power via acoustical signals.

Housing 15 may be generally cylindrical or prismatic and may be formed of an electrically non-conductive material, such as a polymer, glass or ceramic that provides acceptable acoustical and/or RF coupling from power transmitter 70 and to secondary coil 72, respectively, when positioned inside housing 15. In other examples, at least a portion of housing 15 may be formed of an electrically conductive material, e.g., a titanium alloy, stainless steel, or other biocompatible metal. In this case, secondary coil 72 may extend along a non-conductive portion of housing 15 or extend along an outer surface of housing 15 to promote efficient RF coupling between coil 72 and the external, primary coil 48. In some examples, housing 15 is formed from a special grade of titanium that allows RF coupling through housing 15 to coil 72. Housing 15 may be coated or partially coated with a non-conductive coating such as parylene or other material.

In some examples, housing 15 may carry one or more housing-based electrodes 80. Sensing extension 16 is shown extending from housing distal end 50. An electrode 80 may be carried by the housing proximal end 52, as either an exposed portion of an electrically conductive housing 15 or as a tip, button or ring electrode mounted along proximal housing end 52. Electrode 80 may be coupled to sensing module 62 via an electrical feedthrough or may be an electrically conductive portion of housing 15 serving as a ground or anode electrode. For example housing 15 may be formed of a titanium alloy with an insulating coating such as a parylene coating having an opening exposing electrode 80. In other examples, one or more exposed, electrically conductive portions of housing 15 may be provided as one or more housing-based electrodes that are selectable by sensing module 62 in any combination with the sensing extension electrodes 82, 84, and 86 to form a sensing electrode vector for acquiring cardiac electrical signals.

Sensing extension 16 includes an extension body 18 carrying three electrodes 82, 84, and 86 in the example shown. Electrodes 82, 84, and 86 may be ring electrodes, short coil electrodes, plate electrodes or the like. The distal-most electrode 86 may be a hemispherical tip electrode or a helical or hook type electrode providing fixation of sensing extension distal end 19. While three electrodes are shown along sensing extension 16, it is recognized that less than three or more than three electrodes may be carried by sensing extension 16. Extension body 18 includes one or more lumens through which electrical conductors extend from a respective electrode 82, 84 or 86 to a respective electrical feedthrough extending across housing 15 and providing electrical connection to sensing module 86. In the example shown, a housing based electrode 80 is shown at the proximal end of housing 15. In other examples, one or more electrodes 82, 84 and 86 may be coupled to housing 15 when formed of an electrically conductive material and serve as a return anode or ground in the electrical sensing vector without requiring an electrical feedthrough at distal housing end 15.

Sensing module 62 may include switching circuitry for selecting a sensing electrode vector from among the available electrodes 80, 82, 84, and 86. Switching circuitry may include a switch array, switch matrix, multiplexer, or any other type of switching device suitable to selectively couple the selected electrodes to a sense amplifier or other cardiac event detection circuitry included in sensing module 62. Sensing module 62 may include one or more sensing channels to enable monitoring of one or more cardiac electrical signals simultaneously. Each sensing channel may include an input filter and preamplifier for receiving a cardiac electrical signal via the selected sensing electrode vector, a sense amplifier or other cardiac event detector for sensing cardiac events such as P-waves or R-waves, e.g., based on an auto-adjusting threshold crossing of the cardiac electrical signal.

Sensing extension body 18 is shown having a preformed shape including multiple bends or curves so that electrodes 82, 84 and 86 are positioned along different sensing vectors. For example, sensing module 62 may be selectively coupled to electrodes 82 and 86 for sensing a cardiac electrical signal along vector 83. Alternatively, sensing module 62 may be selectively coupled to electrodes 82 and 84 for sensing a cardiac electrical signal along vector 85. In yet another example, electrodes 84 and 86 may be selected for sensing along vector 87. Sensing extension body 18 may curve in approximately a sine wave or "C" shape and may curve or bend in two or three dimensions in order to position electrodes 82, 84 and 86 along at least two different sensing vectors, which may be three orthogonal sensing vectors. The resulting sensing vectors used when housing-based electrode 80 is selected with sensing extension-based electrode 84 is along a different vector than vectors 83, 85 or 87 providing a fourth possible sensing vector. Different electrode spacing and different sensing vectors allow for an optimal sensing electrode combination to be selected for sensing a cardiac electrical signal and identifying cardiac events, e.g., P-waves and R-waves.

Sensing module 62 may pass a cardiac sensed event signal to control module 60 upon sensing a cardiac event, such as a P-wave sensed event signal or an R-wave sensed event signal. Sensing module 62 may additionally include an analog-to-digital converter for providing a digitized ECG signal to control module 60 for performing morphology analysis or other event detection algorithms for detecting and identifying P-waves and R-waves from the cardiac electrical signal.

Sensing module 62 may further be configured to detect pulses delivered by pulse delivery device 100. Detection of pulses delivered by pulse delivery device 100 may be used for feedback in controlling the power transmitted by sensing device 14 and the timing of the power transmission. In some examples, sensing module 62 may be configured to detect an evoked response for confirming cardiac capture by delivered pulses such that power being transmitted may be adjusted up or down as needed.

In some cases, sensing module 62 is configured to detect pulses delivered by pulse delivery device 100 when power transmitter 72 is transmitting a power transmission signal, e.g., an ultrasound signal, in a series of multiple, different directions. Power transmitter 72 may be controlled by control module 60 to transmit an ultrasound signal in multiple directions. The ultrasound signal may intentionally be transmitted at a low amplitude so that the power received by pulse delivery device 100 is too low to produce a pulse having an amplitude greater than the cardiac capture threshold, also referred to as a sub-threshold pacing pulse. The pulse delivery device 100 harvests power from the received ultrasound signal and delivers a sub-threshold pacing pulse for each power transmission in the series. Sensing module 62 senses the delivered pulses and may provide control module 62 with a peak amplitude of the pulse produced for each directional ultrasound signal so that control module 62 may determine which direction is optimal for transmitting power to pulse delivery device 100.

For example, if a series of ultrasound signals is transmitted in three to five different directions through control of an ultrasound transducer array included in power transmitter 70, the transmitted signal resulting in the highest pulse delivered by pulse delivery device 100 is identified as being the optimal direction for power transmission. In this way, sensing device 14 is enabled to target the location of pulse delivery device 100 for power transmission. When multiple pulse delivery devices 100 and 102 are present, the targeted directionality for optimal power transmission can be determined for each pulse delivery device. By sending out several "targeting" signals in various directions and sensing the resulting voltage produced by the pulse delivery device 100, sensing device 14 can discern the direction of the pulse delivery device 100 from the sensing device 14, and thus the desired directionality of the power transmission signal. The same electrodes 80, 82, 84 and 86 and circuitry of sensing module 82 used for sensing cardiac electrical signals may be used for detecting delivered pulses to enable determination of the delivered pulse amplitudes and selecting directionality of the power transmission signal.

Control module 60 may include a microprocessor and computer-readable memory or other storage media for implementing and executing software and firmware programs for performing the functions attributed to sensing device 14 herein. As used herein, the term "module" refers to an application specific integrated circuit (ASIC), an electronic circuit, a processor (shared, dedicated, or group) and memory that execute one or more software or firmware programs, a combinational logic circuit, state machine, switching circuitry, or other suitable components that provide the described functionality. The particular form of software, hardware and/or firmware employed to implement the functionality disclosed herein will be determined primarily by the particular system architecture employed in sensing device 14. Providing software, hardware, and/or firmware to accomplish the described functionality in the context of any modern implantable medical device system, given the disclosure herein, is within the abilities of one of skill in the art.

Control module 60 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, control module 60 may include non-transitory computer readable media storing instructions that, when executed by one or more processing circuits, cause control module 60, in combination with sensing module 62, telemetry module 64 and power transmitter 70 to perform various functions attributed to sensing device 14. The non-transitory, computer-readable media storing the instructions may include any of the media listed above.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components.

Control module 60 is configured to receive cardiac electrical signals from sensing module 62 for identifying P-waves and R-waves. Signals received from sensing module 62 may be a logic signal, referred to herein as P-wave sensed event signal indicating the timing of a sensed P-wave, e.g., based on a P-wave sensing threshold crossing of the cardiac electrical signal, or an R-wave sensed event signal, e.g., based on an R-wave sensing threshold crossing of the cardiac electrical signal. Signals received from sensing module 62 may be a digital ECG signal received for additional signal analysis for identifying P-waves and/or R-waves.

Control module 60 is configured to identify cardiac events, e.g., P-waves and R-waves for determining a pacing interval, set the pacing interval in response identifying a P-wave or R-wave, and enable power transmitter 70 to transmit power to pulse delivery device 100 upon expiration of the pacing interval. As such, control module 60 may include a pacing interval timer or counter for determining the expiration of the pacing interval started upon an identified cardiac event. The power may be transmitted for a time duration of a desired pacing pulse delivered by pulse delivery device 100 such that the transmitted power is harvested and delivered as a pacing pulse by pulse delivery device 100 without requiring a battery or charge storage device in pulse delivery device 100. As such, control module 60 may additionally include a pulse duration timer or counter for controlling the duration of time that the power transmitter 70 is enabled to transmit power. In this way, sensing device 14 controls the timing and duration of the pacing pulse as well as the maximum available power that may be harvested for delivering the pacing pulse.

In some examples, power transmitter 70 includes a transmitting induction coil for RF coupling between sensing device 14 and a receiving coil in pulse delivery device 100. Power transmitter 70 may include a voltage regulator or limiter, capacitors, inductors, a rectifier, comparators, amplifiers and other components as needed for receiving a battery voltage signal from battery 66 and producing an electrical current in a transmitting induction coil included in power transmitter 70. Power transmitter 70 may include an RF oscillator tuned to the resonant frequency of the transmitted RF frequency when power transmission is provided as an RF signal. Control module 60, sensing module 62, and/or power transmitter 70 may include protection circuitry to prevent damage from defibrillation energy delivered to patient 12 by another device and to block conduction during such events.

In other examples, power transmitter 70 produces acoustic power transmission signals by delivering a drive signal to an array of ultrasound transducers included in power transmitter 70. An arrangement of system 10 incorporating acoustic power transmission is described below in conjunction with FIG. 6.

In some examples, sensing device 14 includes an accelerometer 66 for sensing patient activity. An accelerometer and associated method for determining a sensor-indicated pacing rate for supporting the patient's metabolic demand is generally disclosed in U.S. Pat. No. 7,031,772 (Condie, et al.), incorporated herein by reference in its entirety. Accelerometer 66 may be a piezoelectric transducer or a MEMS device bonded to an inner surface of housing 15 or incorporated on an internal substrate of an integrated circuit carrying sensing module 62, control module 60 and telemetry module 64. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers used for sensing patient activity and posture are generally described in U.S. Pat. No. 5,593,431 (Sheldon), and U.S. Pat. No. 6,044,297 (Sheldon), both of which are incorporated herein by reference in their entirety.

Control module 60 may be configured to determine an activity count from a signal received from accelerometer 66. The activity count is correlated to the level of patient activity. The activity count is converted to a sensor-indicated pacing rate using a transfer function or look-up table stored in memory included in control module 60 relating activity counts to pacing rate. A pacing rate interval may then be determined based on the sensor-indicated pacing rate. As described below, control module 60 may be configured to identify P-waves and set a pacing interval for controlling pulse delivery device 100 to deliver a ventricular pacing pulse synchronized to the P-wave at a desired atrioventricular (AV) interval. However, when P-waves cannot be identified, or when control module 60 detects atrial fibrillation according to an implemented tachyarrhythmia detection algorithm, sensing device 14 may switch from an atrial synchronous mode of controlling ventricular pacing to a non-synchronized, single chamber rate-responsive pacing mode.

During the non-synchronous, single chamber rate-responsive pacing mode, control module 60 identifies R-waves from signals received from sensing module 62 and sets a pacing interval derived from the activity sensor-indicated pacing rate. Upon expiration of the activity sensor-indicated pacing rate, control module 60 enables power transmitter 70 to transmit power to pulse delivery device 100 to cause ventricular pacing pulse delivery at the desired ventricular pacing rate.

Telemetry module 64 may include a transceiver and antenna for transmitting and receiving radio frequency or other communication frequency signals to and from external device 40 as described above. The telemetry antenna may be included in housing 15 or external to housing 15. In some examples, coil 72 may have a dual function as a telemetry communication antenna and a power receiving coil for recharging battery 66. An example of an implantable medical device system having switchable inductive energy transfer and communication telemetry between external and implanted coils is generally disclosed in U.S. Pat. No. 8,265,770 (Toy, et al.), incorporated herein by reference in its entirety. Another example of a system for communicating with and providing power to an implantable stimulator that includes aspects that may be implemented in system 10 is generally disclosed in U.S. Pat. No. 8,386,048 (McClure, et al.), also incorporated herein by reference in its entirety. Control module 60 may be programmable such that operating parameters, such as sensing electrode vector, sensing thresholds, sensitivity, pacing intervals, parameters used to automatically determine pacing intervals, and power transmission control parameters, are programmable by a user using external device 40.

FIG. 4 is a schematic diagram of sensing device 14 including an alternative example of sensing extension 16'. Sensing extension body 18' includes a single bend 19 for positioning distal tip electrode 84' offset from the central axis of sensing device housing 15 and at an angle relative to proximal ring electrode 82'. Bend 19 may be pre-formed to assume a relaxed position at a ninety degree angle or less relative to the central axis of the proximal portion of sensing extension 18 and housing 15. By providing at least one curve or bend along sensing extension body 18, a sensing vector extending at a desired angle relative to the cardiac axis may be selected between two extension-based electrodes 82' and 84' or between a housing-based electrode 80 and one of the extension-based electrodes 82' and 84' for optimal sensing and identification of P-waves and/or R-waves while maintaining a position of housing 15 relative to pulse delivery device 100 that enables efficient power transfer from sensing device 14 to pulse delivery device 100.

Figure 5:
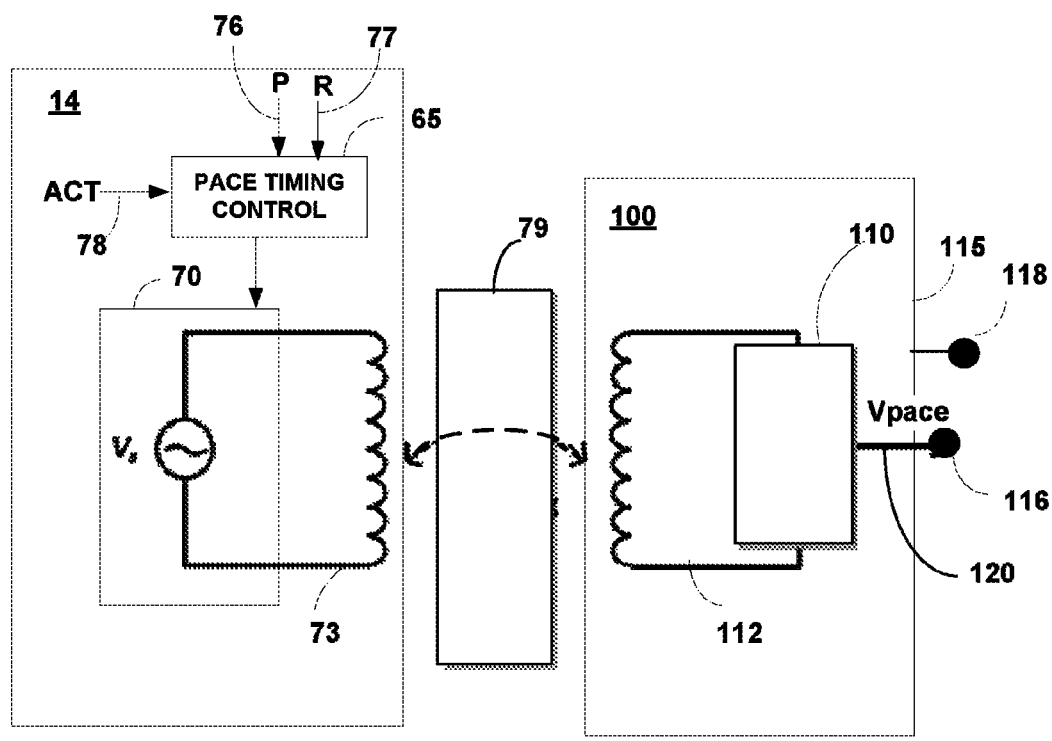
FIG. 5 is a conceptual diagram of the system of FIG. 1 according to one example.

FIG. 5 is a conceptual diagram of sensing device 14 and pulse delivery device 100 according to one example. Pulse delivery device 100 may include a housing 115 enclosing a receiving coil 112 coupled to a power harvesting circuit 110. Power harvesting circuit 110 converts current induced in receiving coil 112 to a pacing pulse delivered on output line 120 to a pacing cathode electrode 116. Pacing cathode electrode 116 may be a housing-based electrode or carried by an extension extending away from housing 115. An exposed electrically conductive portion of housing 115 may serve as a return anode electrode 118.

Harvesting circuit 110 may include a DC blocking element, a voltage regulator or voltage limiter circuit, rectification diodes to convert the energy to a DC signal, a capacitor for smoothing the delivered voltage signal, and a current-activated switch for controlling and coupling current induced in receiving coil 112 to cathode electrode 116. A limiter circuit may limit the maximum voltage amplitude applied to the electrodes 116 and 118 and/or may limit the rate of pulse delivery, i.e., the pacing rate, to avoid a pacing-induced arrhythmia. In some examples, harvesting circuit 110 may include a capacitor that is charged to a pacing pulse voltage by current induced in receiving coil 112 and is discharged across electrodes 116 and 118.

Power is transferred from sensing device 14 to pulse delivery device 100 by mutual coupling of a transmitting coil 73 included in power transmitter 70 and the receiving coil 112 through body tissue 79. A pace timing control module 65, which may be included in control module 60, may receive a P-wave sensed event signal 76 or an R-wave sensed event signal 77 from sensing module 62. Upon receipt of a sensed event signal 76 or 77, pace timing and control module 65 sets a corresponding pacing interval, e.g., an AV interval or a ventricular pacing rate interval as described in greater detail below, and controls power transmitter 70 to apply a voltage signal across transmitting coil 73 upon expiration of the pacing interval. A new pacing interval may be set in response to expiration of the pacing interval and if a subsequent P-wave sensed event signal 76 or subsequent R-wave sensed event signal 77 is not received by pace timing control 65 during the pacing interval, power transmitter 70 is again enabled to transmit power via transmitting coil 73 to pulse delivery device 100 for the next pacing pulse.

In the absence of identifiable P-waves, or the detection of an atrial tachyarrhythmia, pace timing control module 65 may switch to activity-based pacing by setting a pacing rate interval based on a sensor-indicated pacing rate determined using an activity count signal 78 determined from accelerometer 66 (FIG. 3). Operations performed by pacing timing and control module 65 for establishing and controlling pacing intervals are described in greater detail in conjunction with FIG. 7.

Figure 6:
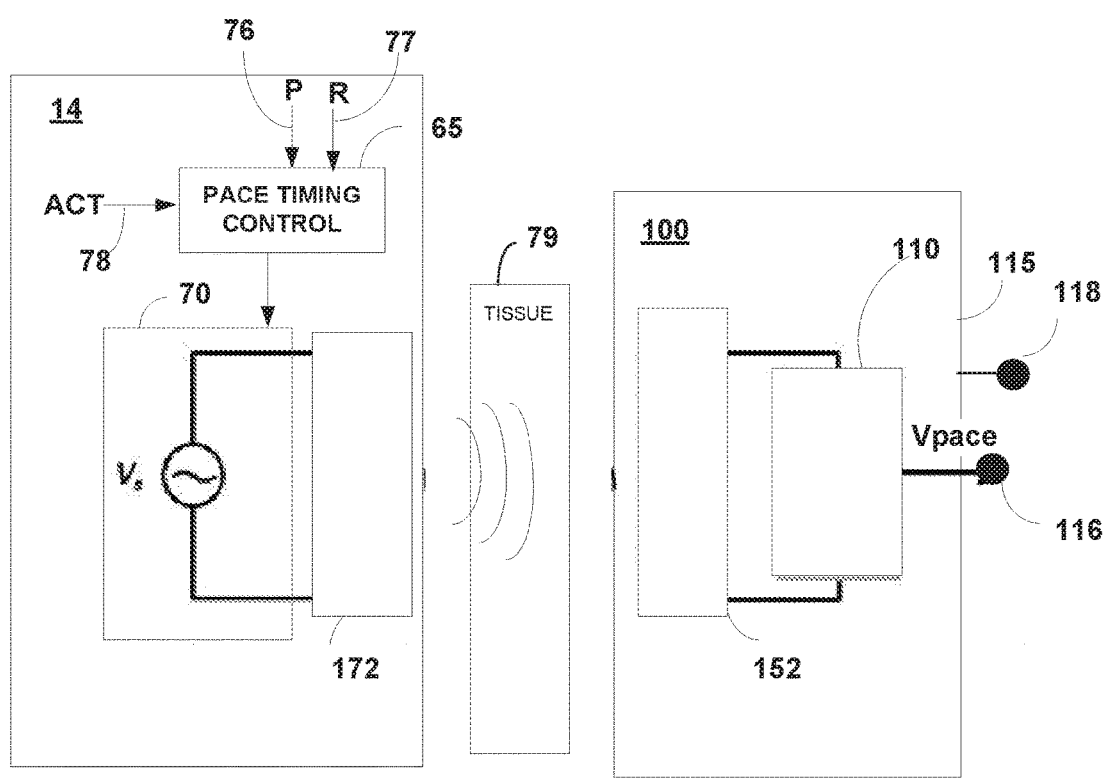
FIG. 6 is a conceptual diagram of an alternative configuration of the system of FIG. 1.

FIG. 6 is a conceptual diagram of an alternative arrangement of sensing device 14 and pulse delivery device 100. In this example, power transmitter 70 applies a drive signal to an array of ultrasound transducers 172 configured to transmit ultrasound through body tissue directed to a receiving ultrasound transducer (or array of receiving transducers) 152 included in pulse delivery device 100. Power transmitter 70 in this example may include an ultrasound oscillator operating in the range of 500 kHz to 10 MHz for example, voltage amplifiers to produce a signal on the order of tens of volts, and phase adjustment circuitry for adjusting the phase of the signal applied to each element of the transducer array.

The array of ultrasound transducers 172 may be controlled to direct an ultrasound signal to each pulse delivery device 100 and 102 (FIG. 1) when multiple delivery devices 100 and 102 are present in the patient and arranged with different relative alignments from sensing device 14. By selectively directing an ultrasound signal to each pulse delivery device, sensing device 14 may control the relative timing or synchrony of pulses delivered by the multiple pulse delivery devices.

Power harvesting circuit 110 converts the current induced in the receiving ultrasound transducer 152 to a pacing pulse delivered to the heart via electrodes 116 and 118. Multiple piezoelectric elements may be included in receiving ultrasound transducer 152 to reduce the dependency of power reception on pulse delivery device orientation. Power harvesting circuit 110 may further include a rectifying diode connected to each piezoelectric element and one or more capacitors for smoothing the received signal. Methods for power transmission and power harvesting for pulse delivery that may be implemented in sensing device 14 are generally disclosed in pre-grant U.S. Publication No. 2013/0282073 (Cowan, et al.), U.S. Pub. No. 2010/0234924 (Willis, et al.), and U.S. Pub. No. 2014/0207210 (Willis, et al.), all of which are incorporated herein by reference in their entirety.

Housing 115 of pulse delivery device 100 may include an acoustic coupling member as generally disclosed in U.S. patent application Ser. No. 14/694,990 (O'Brien, et al.) to promote efficient coupling of acoustical energy transmitted from sensing device 14 to pulse delivery device 100. Other aspects of the methods and apparatus for transmitting and receiving an acoustical signal as disclosed in the '990 application may be implemented in system 10 for transmitting an acoustical signal from sensing device 14 to pulse delivery device 100. U.S. patent application Ser. No. 14/694,990 is incorporated herein by reference in its entirety.

Figure 7:
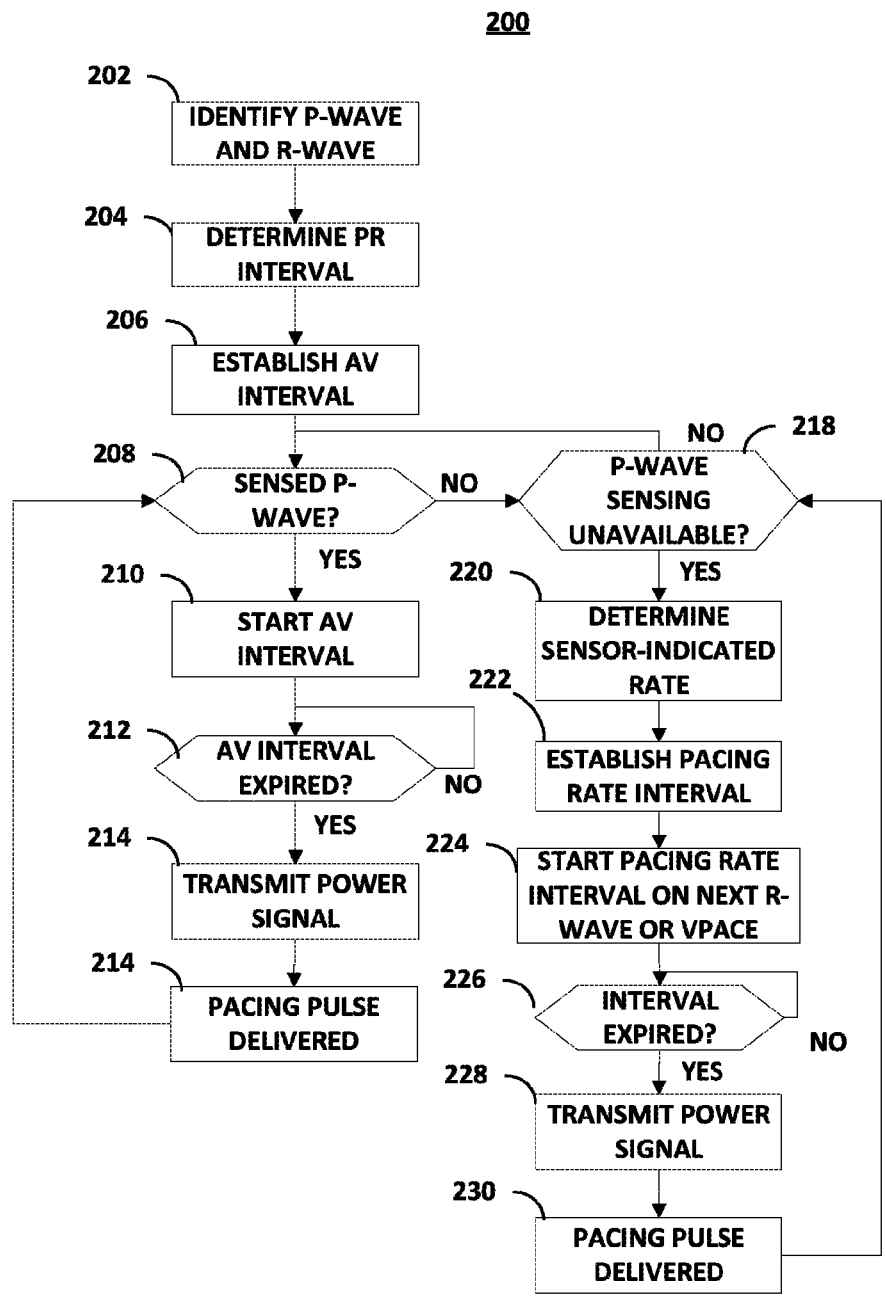
FIG. 7 is a flow chart of a method for delivering cardiac pacing by the system of FIG. 1 according to one example.

FIG. 7 is a flow chart 200 of a method for delivering cardiac pacing by system 10 according to one example. At block 202, control module 60 identifies P-waves and R-waves from signals received from sensing module 62. P-waves and R-waves may be identified based on P-wave sensed event signals and R-wave sensed event signals received from sensing module 62, based on morphological analysis of a digitized ECG signal received from sensing module 62, or a combination of both. Control module 60 determines the PR interval at block 204 as the interval between an identified P-wave and the subsequent R-wave immediately following the P-wave. At block 206, control module 60 establishes an atrioventricular (AV) pacing interval based on the determined PR interval. The AV pacing interval may be set as a portion of the PR interval, e.g., as a percentage of the PR interval or a fixed interval less than the PR interval.

Control module 60 waits for the next sensed P-wave at block 208 and in response to the next sensed P-waves, starts the AV pacing interval at block 210. Upon expiration of the AV pacing interval, "yes" branch of block 212, control module 60 controls power transmitter 70 to transmit a power signal to pulse delivery device 100 at block 214. The pulse delivery device 100 receives the transmitted power signal, harvests power from the received signal and delivers at least a portion of the harvested power as a pacing pulse at block 214. As described above, the power signal starts upon the expiration of the AV interval to control delivery of the pacing pulse at the desired AV interval. Power transmitter 70 transmits the power signal is a time duration that is equal to the desired pacing pulse width in some examples. Upon termination of the power signal, the pacing pulse is also terminated. Control module 60 returns to block 208 to wait for the next sensed P-wave.

Sensing device 14 may be configured to distinguish between intrinsic P-waves and R-waves and atrial and ventricular pacing pulses that are delivered by another device implanted in patient 12, e.g., a dual chamber pacemaker, or evoked depolarizations caused by pacing pulses delivered by another device. A different PR interval may be determined for intrinsic PR intervals than for paced PR intervals (atrial and/or ventricular paced PR intervals). One PR interval may be determined and a corresponding AV pacing interval established when both the P and the R are intrinsic, and a different PR interval may be determined and corresponding AV pacing interval established when the P or the R are paced events, for example when a dual chamber device is delivering RA and RV pacing pulses. In both cases, the AV pacing interval is set to cause pulse delivery device 100 to deliver an LV pacing pulse to increase the likelihood of fusion between RV and LV activations.

In one example, if sensing module 62 is sensing intrinsic R-waves control module 60 is setting a first AV interval to control power transmission for timing of the LV pacing pulse delivered by pulse delivery device 100. If RV pacing begins, by another implanted device, sensing module 62 and control module 60 may identify the RV pacing pulses adjust the AV pacing interval to a second AV interval to maintain pacing pulse delivery in the LV by pulse delivery device 100 at a time relative to the RV pacing pulse delivered by another device to promote fusion of the RV and LV activations. Likewise, if the RV is being paced by another device and pacing stops such that intrinsic R-waves are again sensed by sensing module 62, control module 60 may adjust the AV pacing interval back to the first AV interval for proper timing of the LV pacing pulse to maintain fusion.

If a P-wave is not sensed, "no" branch of block 208, control module 60 may determine whether P-wave sensing is available at block 218. For example, if P-waves have not been identified for a predetermined interval of time or for a predetermined number of successive R-waves, P-wave sensing may be lost. If an atrial tachyarrhythmia detection algorithm is implemented in sensing device 14 and an atrial tachyarrhythmia is being detected, e.g., atrial fibrillation, P-wave sensing is unavailable for synchronizing ventricular pacing. In another example, if sensed P-waves exceed a maximum atrial-tracking ventricular pacing rate, control module 60 may determine that P-wave sensing is unavailable for the purposes of controlling ventricular pacing pulses synchronized to identified P-waves. If control module 60 determines that P-wave sensing is unavailable at block 218, the pace timing control module 65 switches from controlling power transmission in an atrial-synchronized ventricular pacing mode that uses the established AV pacing interval to an activity-based ventricular pacing mode that uses a ventricular pacing rate interval without tracking of the atrial rate.

At block 220, control module 60 determines a sensor-indicated pacing rate based on a signal from accelerometer 66. It is recognized that other patient activity signals could be used for determining a sensor-indicated pacing rate in addition to or in place of an activity count determined from a signal from accelerometer 66. For example, impedance-based respiration rate, patient posture or other signals indicative of patient activity and metabolic demand may be used for determining a sensor indicated pacing rate at block 220.

Control module 60 establishes a pacing rate interval at block 222 based on the sensor indicated pacing rate. The pacing rate interval may be determined based on a transfer function relating pacing rate to activity counts determined from the accelerometer signal and other control parameters which may be used to control how rapidly (e.g., over how many cardiac cycles) the pacing rate interval is shortened (rate acceleration) or how rapidly the pacing rate interval is increased (rate deceleration) in response to a change in the sensor-indicated pacing rate.

At block 224, control module 60 starts the established pacing rate interval on the next sensed R-wave. Upon expiration of the pacing rate interval ("yes" branch of block 226), control module 60 controls the power transmitter 70 to transmit a power signal to pulse delivery device 100 at block 228. Pulse delivery device 100 receives the power signal at block 230 and harvests the signal for delivering the ventricular pacing pulse. As described above, the power signal is transmitted for the desired pacing pulse duration in some examples.

After delivering the pacing pulse, control module 60 restarts the next pacing rate interval to maintain the left ventricular pacing rate at the desired sensor-indicated pacing rate, asynchronous with atrial activity. However, control module 60 may monitor the cardiac electrical signals to determine when P-wave sensing becomes available again at block 218. If P-wave sensing is still unavailable, the sensor-indicated rate is updated at block 220 so that the pacing rate interval may be adjusted as needed on the next pacing cycle. If a pacing rate interval was started upon transmission of the last power signal, the pacing rate interval continues running until it expires at block 226. If an R-wave is sensed during the pacing rate interval, the pacing rate interval may be restarted at block 224.

If P-wave sensing returns, "no" branch of block 218, sensing device 14 returns to the atrial-synchronized ventricular pacing mode by starting the AV interval at block 210 in response to a P-wave sensed at block 208. For example, if a P-wave is sensed during a pacing rate interval, control module 60 may disable setting the pacing rate interval and re-enable setting the AV interval. It is to be understood that the PR interval may be re-determined periodically to update the established AV interval. In some examples, a sensor-indicated rate is not determined when atrial-synchronized ventricular pacing is enabled to conserve battery power. The sensor-indicated rate may be determined only when P-wave sensing is determined to be unavailable for the purposes of delivering atrial-synchronous ventricular pacing. In other examples, the sensor-indicated rate may be determined throughout atrial-synchronized ventricular pacing using the established AV interval such that when P-wave sensing becomes unavailable or atrial-tracking of the ventricular pacing rate is undesirable, the control module 60 can immediately switch to using a pacing rate interval set based on the currently determined sensor-indicated pacing rate without waiting for a sensor-indicated pacing rate to be determined.

If system 10 includes both pulse delivery devices 100 and 102 deployed for delivering pacing pulses in both the LV and the RV, respectively, sensing device 14 may establish a VV delay for controlling the relative timing of pulse delivery to the RV and LV. If only pulse delivery device 100 is present, R-waves sensed when P-wave sensing is unavailable may be used to start a VV pacing interval for controlling power transmission to pulse delivery device 100. For example, the activity-based ventricular pacing rate interval may be set for controlling when power is transmitted to pulse delivery device 100 for causing a pacing pulse to be delivered to the LV. If an R-wave is sensed earlier than the expiration of the pacing rate interval, however, the sensing device 14 may immediately transmit a power signal in response to the sensed R-wave, or transmit a power signal at a desired W delay after the sensed R-wave, to attempt to achieve fusion between the RV and LV. If R-waves (or RV pacing pulses delivered by another device) are sensed prior to expiration of the pacing rate interval for a predetermined number of pacing rate intervals, the pacing rate interval may be adjusted to a shortened pacing rate interval in an attempt to establish fusion between the RV and LV by overtaking or matching an intrinsic rate in the case of sensed R-waves or match a paced rate in the case of sensed RV pacing pulses.

Thus, an apparatus and method have been presented in the foregoing description for delivering cardiac pacing with reference to specific examples. It is appreciated that various modifications to the referenced examples may be made, including modifying the order of steps performed and/or modifying the combinations of operations shown in the drawings presented herein, without departing from the scope of the following claims.

The invention claimed is:

1. An implantable medical device system for delivering cardiac pacing, comprising:
 a first device comprising a power transmitter, sensing circuitry, a control module, a first housing enclosing the power transmitter, the sensing circuitry and the control module, a plurality of sensing electrodes, and an extra-cardiovascular sensing extension extending from the first housing and carrying at least one of the plurality of sensing electrodes, the control module configured to:
  identify a first cardiac event by identifying a P-wave from a cardiac electrical signal received by the sensing circuitry via the plurality of sensing electrodes,
  identify a second cardiac event by identifying an R-wave;
  determine an interval between the P-wave and the R-wave; and
  set a first pacing interval to be less than the interval between the P-wave and the R-wave in response to identifying the first cardiac event, and
  control the power transmitter to transmit power upon expiration of the first pacing interval; and
 a second device comprising a pacing electrode pair, a second housing, and a power receiver enclosed by the second housing, the power receiver coupled to the first pacing electrode pair, the first pacing electrode pair carried by the second housing;
 wherein the power receiver is configured to receive the transmitted power and deliver at least a portion of the received power to a patient's heart via the first pacing electrode pair.

2. The system of claim 1, wherein the extension comprises a proximal end coupled to the first housing, a distal end extending away from the first housing, and a body extending from the proximal end to the distal end, the body having at least one bend, at least one of the plurality of sensing electrodes carried by the body distal to the at least one bend.

3. The system of claim 2, wherein the extension comprises a second electrode of the plurality of sensing electrodes carried by the body proximal to the at least one bend.

4. The system of claim 1, wherein the first device comprises a third electrode of the plurality of electrodes carried by one of the first housing and the sensing extension body, wherein the first electrode and the third electrode define a first sensing vector and the second electrode and one of the first electrode and the third electrode define a second sensing vector different than the first sensing vector.

5. The system of claim 1, wherein the extra-cardiovascular sensing extension comprises a proximal end coupled to the first housing, a distal end extending away from the first housing, and a body extending from the proximal end to the distal end, the body comprising a curved portion between the proximal end and the distal end, a first sensing electrode of the plurality of sensing electrodes carried along the curved portion, a second sensing electrode of the plurality of sensing electrodes carried proximal to the curved portion, and a third sensing electrode of the plurality of sensing electrodes carried distal to the curved portion, the first, second and third sensing electrodes defining at least two different sensing electrode vectors.

6. The system of claim 1, wherein at least a portion of the extra-cardiovascular sensing extension is configured to be deployed along an intercostal space of the patient.

7. The system of claim 1, wherein at least a portion of the extra-cardiovascular sensing extension is configured to be deployed substernally.

8. The system of claim 1, wherein:
 the second device further comprises an activity sensor; and
 the control module is configured to:
  determine a second pacing interval based on a signal from the activity sensor;
  start the second pacing interval upon identifying an R-wave; and
  control the power transmitter to transmit power in response to expiration of the second pacing interval.

9. The system of claim 8, wherein the control module is further configured to:
 determine whether identifying of the first cardiac event is unavailable;
 disable setting the first pacing interval in response to determining that identifying the first cardiac event is unavailable; and
 enable setting the second pacing interval in response to disabling setting the first pacing interval.

10. The system of claim 9, wherein the control module is configured to:
 identify a next first cardiac event during the second pacing interval;
 re-enable setting the first pacing interval in response to identifying the next first cardiac event; and
 disable setting the second pacing interval in response to re-enabling setting the first pacing interval.

11. The system of claim 1, wherein the power transmitter comprises a first coil for inductive power transmission and the power receiver includes a second coil for receiving the transmitted power.

12. The system of claim 1, wherein the power transmitter comprises a transmitting ultrasound transducer for transmitting the power and the power receiver includes a receiving ultrasound transducer for receiving the transmitted power.

13. The system of claim 1, wherein the second device is deployed to deliver at least a portion of the transmitted power to evoke a depolarization of the left ventricle.

14. The system of claim 1, further including a third device comprising a second pacing electrode pair, a third housing, and a second power receiver enclosed by the third housing, the second power receiver coupled to the second pacing electrode pair, the second pacing electrode pair carried by the third housing;
  wherein the third device is configured to receive power transmitted by the second device and deliver at least a second portion of the transmitted power to the patient's heart via the second electrode pair.

15. The system of claim 14, wherein:
the second device is configured to be deployed for delivering the portion of the transmitted power via the first pacing electrode pair to a first location of the patient's heart;
the third device is configured to be deployed for delivering the second portion of the transmitted power via the second pacing electrode pair to a second location of the patient's heart spaced apart from the first location.

16. The system of claim 15, wherein the first location is along a left ventricle of the heart and the second location is along a right ventricle of the patient heart.

17. A method for delivering cardiac pacing by an implantable medical device system, comprising:
receiving a cardiac electrical signal via a plurality of sensing electrodes coupled to sensing circuitry of a first device, at least one of the plurality of sensing electrodes carried by an extra-cardiovascular sensing extension extending from the first device;
identifying by a control module of the first device a first cardiac event by identifying a P-wave from the cardiac electrical signal;
identifying a second cardiac event by identifying an R-wave;
determining an interval between the P-wave and the R-wave;
setting a first pacing interval to be less than the interval between the P-wave and the R-wave in response to identifying the first cardiac event;
controlling a power transmitter of the first device to transmit power upon expiration of the first pacing interval;
receiving the transmitted power by a power receiver of a second device; and
delivering at least a portion of the received power to a patient's heart via a first pacing electrode pair of the second device coupled to the power receiver.

18. The method of claim 17, wherein receiving the cardiac electrical signal comprises receiving the signal using one of the plurality of sensing electrodes carried distal to a bend of a body of the sensing extension, the body extending from a proximal end coupled to a housing of the first device to a distal end extending away from the housing.

19. The method of claim 18, wherein receiving the cardiac electrical signal comprises receiving the signal using a second electrode of the plurality of sensing electrodes carried by the body proximal to the bend.

20. The method of claim 17, wherein receiving the cardiac electrical signal comprises selecting one of a first sensing electrode vector and a second sensing electrode vector for receiving the cardiac electrical signal,
  wherein the first sensing electrode vector is defined by a first electrode carried by the sensing extension body and a second electrode carried by a housing of the first device,
  the second sensing electrode vector is defined by a third electrode carried by the sensing extension body and one of the first electrode and the third electrode.

21. The method of claim 17, wherein receiving the cardiac electrical signal comprises selecting one of a first sensing electrode vector and a second sensing electrode vector for receiving the cardiac electrical signal,
  wherein the first sensing electrode vector comprises a first electrode carried by a curving portion of a body of the sensing extension and a second electrode carried proximal to the curving portion of the sensing extension body;
  the second sensing electrode vector comprises one of the first electrode and the second electrode and a third electrode carried distal to the curving portion of the sensing extension body.

22. The method of claim 17, further comprising deploying the extra-cardiovascular sensing extension along an intercostal space of the patient for receiving the cardiac electrical signal.

23. The method of claim 17, further comprising deploying at least a portion of the extra-cardiovascular sensing extension substernally.

24. The method of claim 17, further comprising:
determining a second pacing interval based on a signal from an activity sensor;
starting the second pacing interval upon identifying an R-wave; and
controlling the power transmitter to transmit power in response to expiration of the second pacing interval.

25. The method of claim 24, further comprising:
determining whether identifying of the first cardiac event is unavailable;
disabling setting the first pacing interval in response to determining that identifying the first cardiac event is unavailable; and
enabling setting the second pacing interval in response to disabling setting the first pacing interval.

26. The method of claim 25, further comprising:
identifying a next first cardiac event during the second pacing interval;
re-enabling setting the first pacing interval in response to identifying the next first cardiac event; and
disabling setting the second pacing interval in response to re-enabling setting the first pacing interval.

27. The method of claim 17, wherein transmitting the power comprises applying current to a first coil for inductive power transmission and receiving the transmitted power comprises harvesting current induced in a second coil by the current applied to the first coil.

28. The method of claim 17, wherein transmitting the power comprises activating an ultrasound transducer and receiving the power comprises harvesting power includes harvesting current induced in a receiving ultrasound transducer.

29. The method of claim 17, wherein delivering at least a portion of the received power to a patient's heart via the first pacing electrode pair comprises delivering at least a portion of the transmitted power to evoke a depolarization of the left ventricle.

30. The method of claim 17, further comprising:
receiving at least a portion of the transmitted power by a third device having a second pacing electrode pair; and
delivering at least a second portion of the transmitted power to the patient's heart via the second electrode pair.

31. The method of claim 30, further comprising:
deploying the second device having the first pacing electrode pair to a first location of the patient's heart; and
deploying the third device having the second pacing electrode pair to a second location of the patient's heart spaced apart from the first location.

32. The method of claim 31, wherein:
deploying the second device to the first location comprises deploying the second device along a left ventricle of the patient's heart; and
deploying the third device to the second location comprises deploying the third device along a right ventricle of the patient's heart.

33. A non-transitory, computer-readable medium comprising a set of instructions which when executed by a control module of an implantable medical device system comprising a first device and a second device cause the system to:
receive a cardiac electrical signal via a plurality of sensing electrodes coupled to sensing circuitry of the first device, at least one of the plurality of sensing electrodes carried by an extra-cardiovascular sensing extension extending from the first device;
identify by a control module of the first device a first cardiac event by identifying a P-wave from the cardiac electrical signal;
identifying a second cardiac event by identifying an R-wave;
determining an interval between the P-wave and the R-wave;
setting a first pacing interval to be less than the interval between the P-wave and the R-wave in response to identifying the first cardiac event;
control a power transmitter of the first device to transmit power upon expiration of the first pacing interval;
receive the transmitted power by a power receiver of the second device; and
deliver at least a portion of the received power to a patient's heart via a pacing electrode pair of the second device coupled to the power receiver.

34. An implantable medical device comprising:
a power transmitter,
sensing circuitry,
a control module,
a housing enclosing the power transmitter, the sensing circuitry and the control module,
a plurality of sensing electrodes, and
an extra-cardiovascular sensing extension extending from the housing and carrying at least one of the plurality of sensing electrodes, the control module configured to:
identify a first cardiac event by identifying a P-wave from a cardiac electrical signal received by the sensing circuitry via the plurality of sensing electrodes,
identify a second cardiac event by identifying an R-wave;
determine an interval between the P-wave and the R-wave; and
set a first pacing interval to be less than the interval between the P-wave and the R-wave in response to identifying the first cardiac event, and
control the power transmitter to transmit power for pacing to another device upon expiration of the first pacing interval.

35. The system of claim 34, wherein the extension comprises a proximal end coupled to the first housing, a distal end extending away from the first housing, and a body extending from the proximal end to the distal end, the body having at least one bend, at least one of the plurality of sensing electrodes carried by the body distal to the at least one bend.

36. The system of claim 35, wherein the extension comprises a second electrode of the plurality of sensing electrodes carried by the body proximal to the at least one bend.

37. The system of claim 34, wherein the first device comprises a third electrode of the plurality of electrodes carried by one of the first housing and the sensing extension body, wherein the first electrode and the third electrode define a first sensing vector and the second electrode and one of the first electrode and the third electrode define a second sensing vector different than the first sensing vector.

38. The system of claim 34, wherein the extra-cardiovascular sensing extension comprises a proximal end coupled to the first housing, a distal end extending away from the first housing, and a body extending from the proximal end to the distal end, the body comprising a curved portion between the proximal end and the distal end, a first sensing electrode of the plurality of sensing electrodes carried along the curved portion, a second sensing electrode of the plurality of sensing electrodes carried proximal to the curved portion, and a third sensing electrode of the plurality of sensing electrodes carried distal to the curved portion, the first, second and third sensing electrodes defining at least two different sensing electrode vectors.

39. The system of claim 34, wherein the power transmitter comprises a first coil for inductive power transmission.

40. The system of claim 34, wherein the power transmitter comprises a transmitting ultrasound transducer for transmitting the power.

* * * * *